United States Patent [19]
Routh

[11] Patent Number: 5,606,972
[45] Date of Patent: Mar. 4, 1997

[54] ULTRASONIC DOPPLER MEASUREMENT OF BLOOD FLOW VELOCITIES BY ARRAY TRANSDUCERS

[75] Inventor: Helen F. Routh, Seattle, Wash.

[73] Assignee: Advanced Technology Laboratories, Inc., Bothell, Wash.

[21] Appl. No.: 513,465

[22] Filed: Aug. 10, 1995

[51] Int. Cl.[6] .................................................. A61B 8/06
[52] U.S. Cl. ............................................... 128/661.09
[58] Field of Search ........................ 128/661.07–661.1; 73/861.25

[56] References Cited

U.S. PATENT DOCUMENTS

| | | | |
|---|---|---|---|
| 4,416,286 | 11/1983 | Iinuma et al. | 128/663 |
| 4,790,322 | 12/1988 | Iinuma | 128/661 |
| 4,790,323 | 12/1988 | Leavitt et al. | 128/661 |
| 4,937,797 | 6/1990 | Snyder et al. | 367/138 |
| 4,972,838 | 11/1990 | Yamazaki | 128/661 |
| 5,035,245 | 7/1991 | Nakamura et al. | 128/661.09 |
| 5,105,813 | 4/1992 | Shikata | 128/660 |
| 5,231,573 | 7/1993 | Takamizawa | 364/413 |
| 5,271,404 | 12/1993 | Corl et al. | 128/661.09 |
| 5,375,600 | 12/1994 | Melton, Jr. et al. | 128/661.09 |

Primary Examiner—Francis Jaworski
Attorney, Agent, or Firm—W. Brinton Yorks, Jr.

[57] ABSTRACT

A Doppler signal processor is provided for an ultrasonic diagnostic imaging system which identifies the peak and mean flow velocities by Doppler interrogation of a sample volume within the body. The effects of spectral broadening resulting from the use of an array transducer are compensated by producing a peak velocity value which is a function of the dimension of the array aperture and its relation to the location of the sample volume. Mean velocity values calculated from received Doppler echoes are combined with an array distortion function to produce accurate mean velocity values. The entire spectrum may be corrected by deconvolving the received signal spectrum with an array distortion function. Alternatively the effects of spectral broadening are compensated by use of Doppler reference signals for each element of the array which are a function of the position of the individual elements in the array aperture.

27 Claims, 5 Drawing Sheets

FIG.4

ULTRASONIC DOPPLER MEASUREMENT OF BLOOD FLOW VELOCITIES BY ARRAY TRANSDUCERS

This invention relates to the measurement of fluid flow velocities in the body using ultrasonic Doppler signal techniques, and in particular to ultrasonic Doppler measurement in the presence of aperture induced spectral broadening effects.

In the ultrasonic Doppler measurement of fluid flow characteristics, waves of returning ultrasonic signals are compared to a phase reference to determine the frequency shift of the returning waves. As the transmitted ultrasonic wave impinges upon flowing material such as blood cells, the movement of the flowing material will impart a Doppler shift to the returning echo signal. This frequency shift, which is commonly measured in kilohertz, translates into the rate of movement or velocity of the blood flow. This Doppler velocity information is conventionally displayed as a continuous spectrum of lines of varying amplitudes in a moving or scrolled display on a video monitor. The information may also be displayed as instantaneous velocities at discrete points in a two dimensional image. Each line or point represents an instantaneous measurement of blood flow. For arterial flow, the spectrum of lines will rise during the systolic phase of the heart cycle and decline to lower levels during the diastolic phase of the heart cycle. As the flow of blood in a vessel or the heart is continuously monitored and interrogated by Doppler ultrasound, the spectrum of systolic and diastolic velocities is continuously displayed and passed before the clinician.

In order to analyze the various disease states of the cardiovascular system it is desirable to calculate a number of parameters from the spectral velocity information. These parameters include peak systolic velocity, minimum diastolic velocity, the systolic/diastolic ratio, the pulsatility index, the velocity time integral, and the time averaged mean velocity of blood flow at a particular site in the body. Many of these parameters are predicated upon identifying peak and mean velocities of blood flow at the measurement site, termed a sample volume. U.S. Pat. No. 5,287,753 describes a technique for continuously determining and displaying the peak and mean velocities of spectral Doppler information in the presence of noise by first determining a noise threshold of received spectral Doppler data. Individual instantaneous measurements, or lines, of Doppler spectral information are analyzed to compare the line information against the noise threshold. The correlation of the threshold and the spectral line information identifies the peak velocity of the spectral line. Mean velocity is calculated as an intensity weighted mean of the spectral line information. The identified peak and mean velocities are displayed in contrasting colors or shades on a continuously updated and displayed frequency versus time spectral display.

It has been found that use of a multielement array transducer with a finite aperture can cause a variation to occur in the received Doppler data. This is because the paths between the sample volume and the different elements of the array transducer will exhibit different angles in relation to the direction of blood flow. Since the Doppler shift is a function of the angle of incidence between the ultrasound path and the flow direction, each transducer element will detect a slightly different shift, depending upon the angle of incidence of its signal. When the signals from the transducer elements are combined and processed to recover the Doppler shift, a range of Doppler shifts will be detected, which will be translated into a corresponding range of blood flow velocities. The broadening of the range of frequency shifts and corresponding velocities caused by these angular differences are herein termed "spectral broadening." It would be desirable to be able to eliminate these spectral broadening effects and, in particular, to be able to produce accurate Doppler measurements of peak and mean flow velocities in the presence of these effects.

In accordance with the principles of the present invention a technique is provided for making accurate peak and mean ultrasonic Doppler velocity measurements using a multielement transducer. Doppler measurements are made at a sample volume location which exhibits a unique depth and Doppler angle to a nominal ultrasonic beam path and the direction of fluid flow. Echo signals from the active aperture are received and Doppler processed to yield a spectrum of frequency shifts. The peak velocity is determined from the spectrum by correcting the measured peak velocity based upon the smallest Doppler angle of the active aperture of the transducer array.

Since reception of the ultrasonic Doppler signals by a single element in the active aperture would not give rise to spectral broadening, a spectral function can be derived based upon the premise that the spectrum of the received Doppler signals is a convolution of an ideal spectrum and a distortion function resulting from use of an array transducer. Through application of this premise, a mean velocity estimate derived from the received Doppler spectrum is combined with a factor derived from such a distortion function to yield an accurate measure of mean Doppler velocity.

Correction of a complete Doppler spectrum is provided by use of a Doppler reference frequency for each transducer element in the active array which varies with position of the element in the active array. The separate reference frequencies are preferably used during transmission of the ultrasonic beam and during reception of the Doppler echo signals to compensate for spectral broadening effects.

Figure 1:
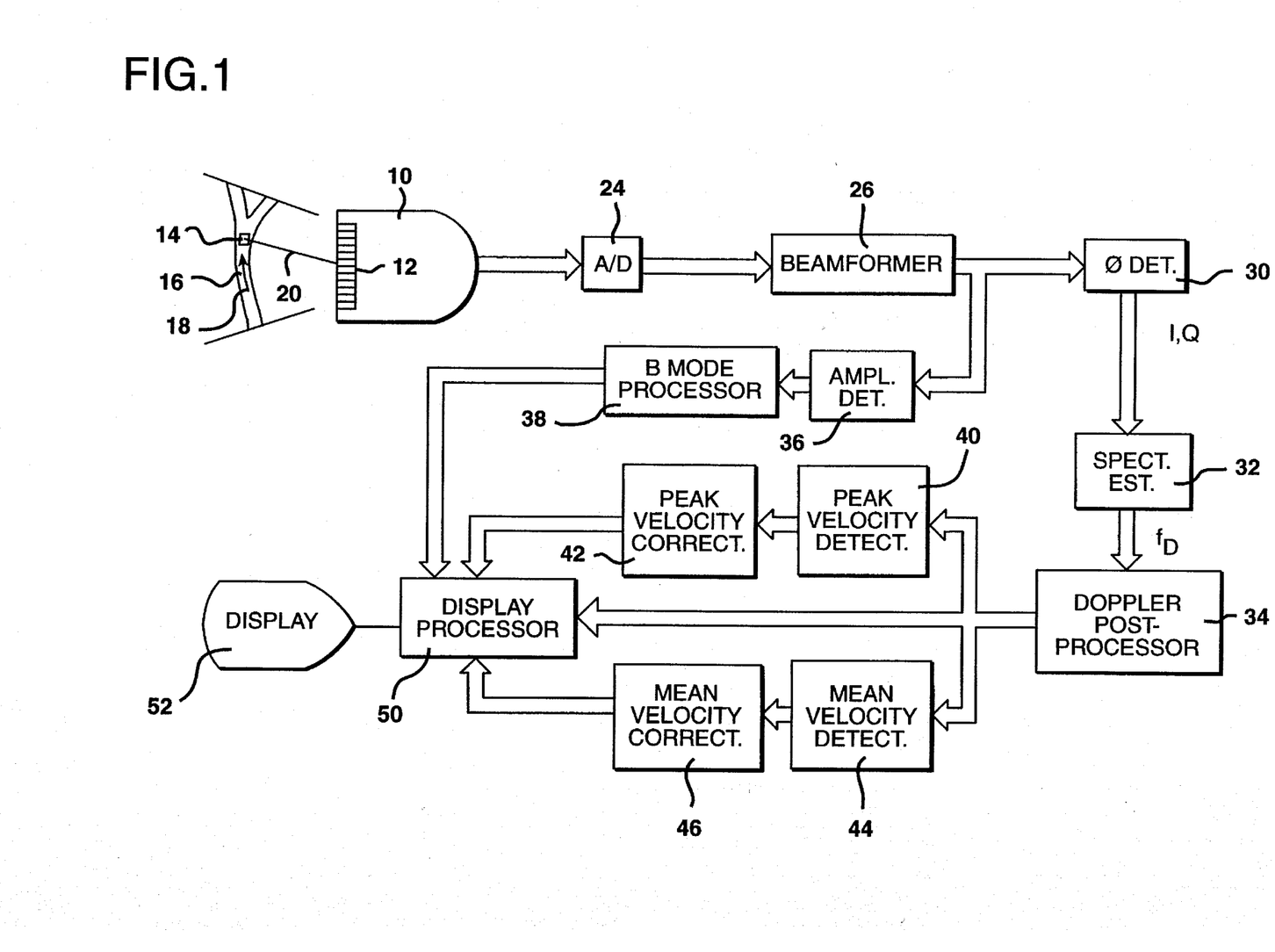
FIG. 1 is a block diagram of an ultrasonic diagnostic imaging system constructed in accordance with the principles of the present invention.

Referring first to FIG. 1, a block diagram of an ultrasonic diagnostic imaging system constructed in accordance with the principles of the present invention is shown. An ultrasonic scanhead 10 including an array transducer 12 transmits ultrasonic Doppler waves along a nominal beam direction 20 to a sample volume 14. The sample volume is positioned in a blood vessel 16 through which blood is flowing in the direction indicated by arrow 18. Echoes returning from blood cells in the sample volume region return to the transducer array and are received by the elements of the array. The echo components received by each transducer element are converted to digital signals by analog to digital converters 24 and the digital echo signals from the individual elements are processed by a beamformer 26 to form a beam of echo signals.

The echo signals are directed along two paths, one for structural image processing and another for Doppler processing. For structural image processing the echo signals are detected by an amplitude detector 36, then processed to form a two dimensional or B mode image by a B mode processor 38. The B mode image signals are provided to a display processor 50 for display of the interior structure of the body, including the blood vessel 16, by a display 52.

In the Doppler processing path the echo signals are detected by a phase detector 30 to produce quadrature I and Q samples for each echo signal. A number of such signal components which have been acquired over time from the sample volume site in the body being diagnosed are applied to a Doppler spectral estimator 32, one form of which is a fast Fourier transform (FFT) processor, which computes the Doppler frequency shift $f_D$ of the received signals. This basic Doppler data is post- (or pre-) processed by a Doppler post processor 34, which further refines the data by techniques such as wall filtering as described in U.S. Pat. No. 5,197,477. Post processing may also include functions such as gain control, or amplitude compression.

The post processed frequency shift estimates $f_D$ are applied to the display processor 50 where the Doppler information is formatted for display as lines of a spectral display or spatial velocity pixels of a color flow display. The Doppler information is also processed to determine the peak and mean velocity values as described in U.S. Pat. No. 5,287,753 or U.S. patent application Ser. No. 08/489,258. As discussed therein, a peak velocity detector 40 may detect the peak velocity by identifying the highest valid frequency in a range of frequency values and a mean velocity detector 44 may detect the mean velocity of a range of values by computation of an intensity weighted mean velocity value.

Since the Doppler signals are transmitted and received by different elements of an array transducer, each element of the array will exhibit its own unique angle between the path of its transmitted and received signal and the blood flow direction. Accordingly, the echo signal component of each transducer element will indicate a slightly different Doppler frequency shift and hence there will be a broadening of the spectral estimates. In accordance with the principles of the present invention the peak velocity values identified by the peak velocity detector 40 are compensated for the effects of this spectral broadening by a peak velocity corrector 42. The effects of spectral broadening on the identified mean velocity values are compensated by a mean velocity corrector 46. The corrected peak and mean velocity values are provided to the display processor 50 where they are displayed quantitatively or in a color flow or spectral Doppler display.

Figure 2:
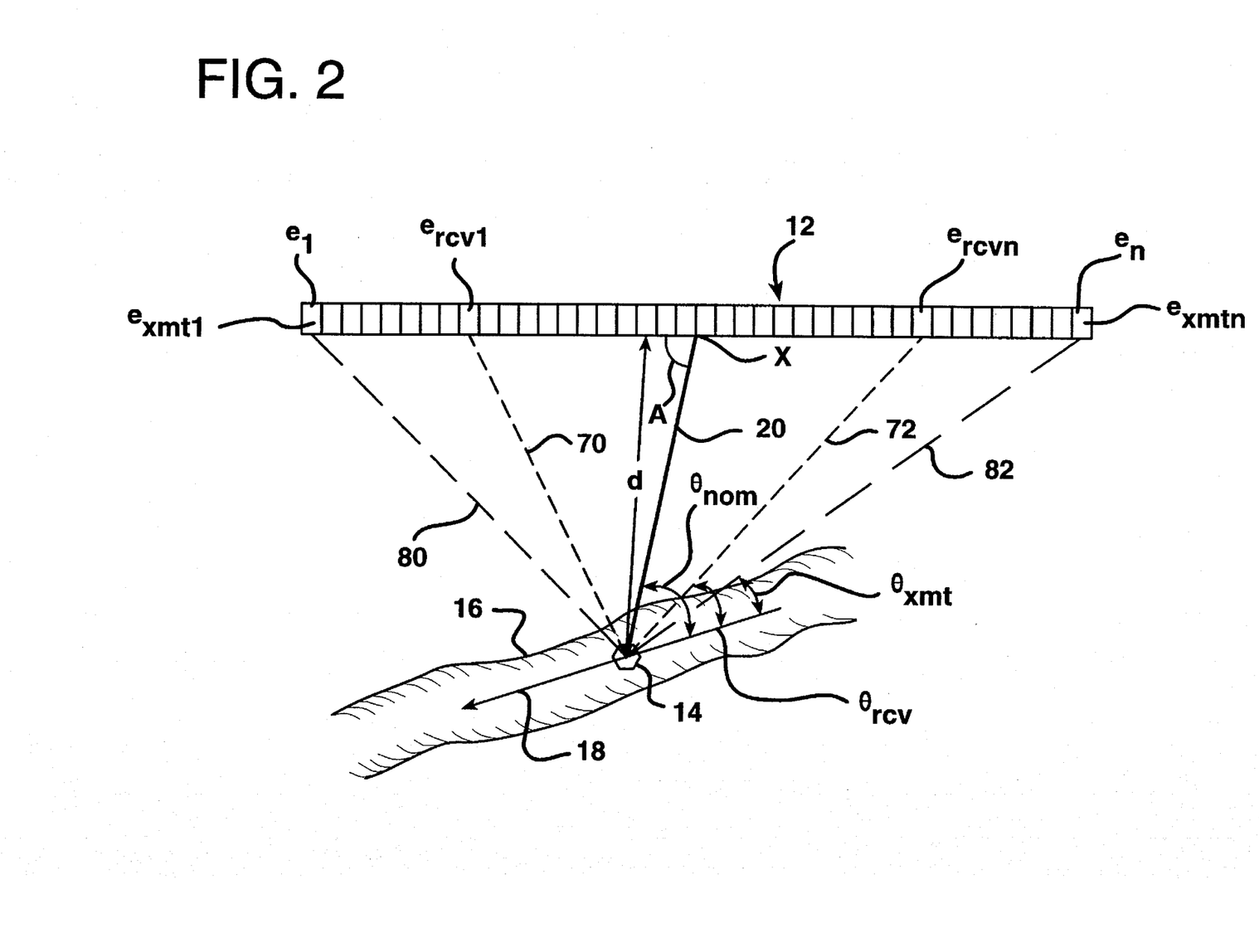
FIG. 2 illustrates the relationships between a transducer array and a sample volume which are used in making velocity corrections in accordance with the principles of the present invention.
Figure 3:
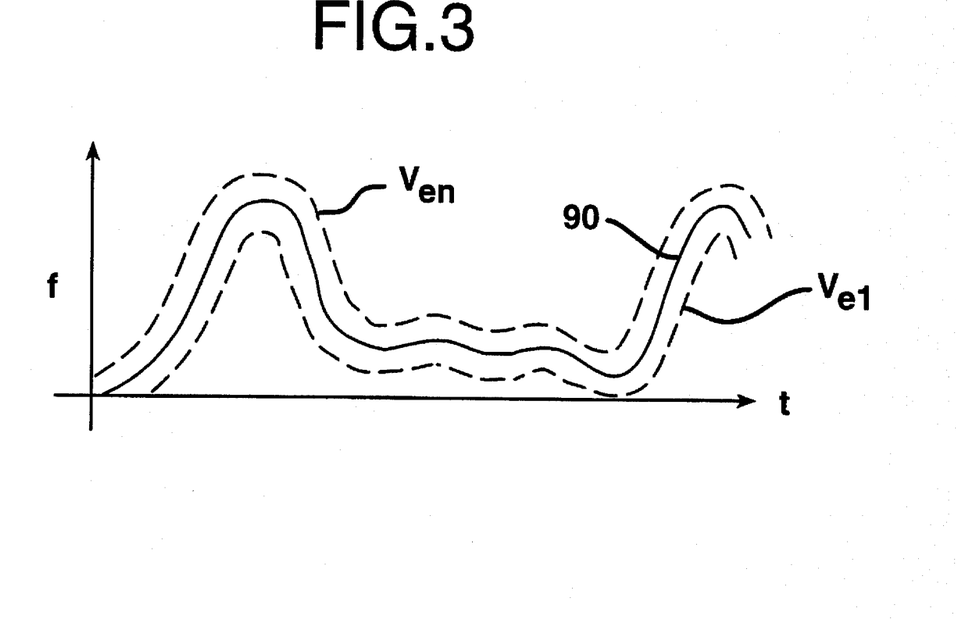
FIG. 3 is a spectral Doppler display illustrating the effects of spectral broadening.
Figure 4:
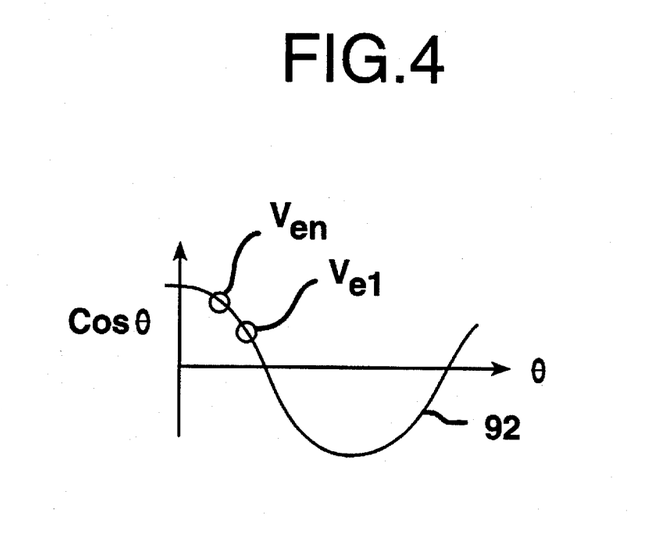
FIG. 4 illustrates the relationship between a Doppler angle and its cosine.

The means by which spectral broadening effects arise and are compensated in accordance with the present invention are understood with reference to FIGS. 2, 3, and 4. FIG. 2 is an enlarged view of the transducer array 12 of the scanhead 10 and the sample volume 14 in blood vessel 16 which is being interrogated by Doppler waves. Echoes returning from the wall structure of the vessel 16 are processed and shown as a structural B mode image of the vessel on the display 52. To interrogate the blood flow characteristics at a point in the vessel a cursor 20 which extends from a point x along the face of the array 12 is displayed on the display screen. The user can steer this cursor to intersect the sample volume site 14 at which Doppler measurements are to be made. The user also places and adjusts a second cursor which indicates the direction of blood flow as shown by arrow 18. The placement of these cursors and their intersection define a number of relationships between the transducer array 12 and the blood flow at the sample volume: a steering angle A between the cursor 20 and the face of the transducer array; a Doppler angle $\theta_{nom}$ between the Doppler steering cursor 20 and the flow direction cursor 18; and the depth d between the face of the array and the sample volume 14.

The problem of spectral broadening resides in the fact that Doppler waves are being transmitted and received from an array of transducer elements, each of which has its own unique steering angle, Doppler angle $\theta$, and distance to the sample volume. If the Doppler waves were transmitted from a single transducer element at point x and were received by only the same element, the problem of spectral broadening would not arise. This is because the Doppler frequency shift is computed by the equation $$f_D = 2v f_o \cos\theta / c \qquad (1)$$

where c is the speed of sound, v is the velocity of blood flow, $f_o$ is the Doppler wave frequency and $\theta$ is the Doppler angle. With a single element there is effectively only one transmit and receive path, that defined by the cursor 20. There is thus only a single Doppler angle, which is $\theta_{nom}$ in FIG. 2.

However, when an array of transducer elements is used, each has its own unique Doppler angle. In FIG. 2 it may be seen that there is a very small acute angle between dashed line 82 extending from element $e_n$ and the blood flow cursor 18 (shown as $\theta_{xmt}$ in the drawing), whereas there is an almost orthogonal angle between dashed line 80 extending from element $e_1$ and the blood flow cursor 18. Thus the two end elements of the array will contribute significantly different $\cos\theta$ values to the frequency shift calculation, as will the intervening transducer elements, resulting in a spread of computational results.

The results of spectral broadening on a spectral Doppler display are shown in FIG. 3. In this drawing the correct peak blood flow velocities as a function of time are represented by the solid waveform 90. The contribution to the peak velocity from the leftmost transducer element $e_1$ of the array is indicated by dashed waveform $V_{e1}$. The contribution to the peak velocity from the rightmost transducer element $e_n$ of the array is indicated by dotted waveform $V_{en}$. Other elements of the array will contribute their own peak value components within this spread of values. Because the velocity is derived by a cosine function, the highest velocity will result from the smallest Doppler angle as represented in FIG. 4.

Compensating for spectral broadening can be further complicated by the use of different transmit and receive apertures. In the example of FIG. 2 the Doppler waves are transmitted from the full array from element $e_1$ to element $e_n$ and their beam paths will be in the range bounded by dashed lines 80 and 82. In the example the returning Doppler echoes are received by elements $e_{rcv1}$ through $e_{rcvn}$, with beam paths bounded by dashed lines 70 and 72. The received signals will be a function of the Doppler angles of both the elements of the transmit aperture and of the receive aperture.

In accordance with the principles of the present invention the peak velocity corrector 42 provides compensation based upon the transmit aperture, the receive aperture, the sample volume depth d, the nominal Doppler angle $\theta_{nom}$, and the steering angle A. This is done by multiplying each detected peak velocity by the function $$\frac{2\cos\theta_{nom}}{(\cos\theta_{rcv} + \cos\theta_{xmt})} \qquad (2)$$

where $\cos\theta_{rcv}$ and $\cos\theta_{xmt}$ are the cosines of the smallest angles between a beam direction from an element of the receive and transmit apertures, respectively, and the blood flow vector 18. In the example of FIG. 2 the most acute angle between a transmit beam path of the transmit aperture $e_1$–$e_n$ and the blood flow vector 18 is angle $\theta_{xmt}$ between cursor 18 and the path indicated by dashed line 82 between element $e_{xmtn}$ and the sample volume; the angle between every other transmit path along the transmit aperture and the blood flow vector is greater. The most acute angle between a receive beam path of the receive aperture $e_{rcv1}$–$e_{rcvn}$ and the blood flow vector 18 is angle $\theta_{rcv}$ between cursor 18 and the path indicated by dashed line 72 between element $e_{rcvn}$ and the sample volume; the Doppler angle of every other receive path along the transmit aperture is greater. These minimal Doppler angles contribute the greatest peak velocity values to the peak velocity computational result.

The values for peak velocity compensation equation (3) are readily determined from the settings of cursors 18 and 20 by the user. The numerator term is seen to be defined by the angle between the cursors and is available from the ultrasound system once the cursors have been positioned. The transmit and receive apertures are either system presets or preset by the user prior to the examination and, in either case, are known at the time of the Doppler examination. Hence the angular relationships between the elements used in the apertures and the bloodflow cursor 18 can be readily identified and the smallest angle to each aperture determined.

Equation (2) is seen to provide compensation based upon the five previously identified factors. The $\cos\theta_{xmt}$ term is a function of the transmit aperture, the $\cos\theta_{rcv}$ term is a function of the receive aperture, all three cosine terms are related to the sample volume depth and the Doppler steering angle, and the nominal Doppler angle is the numerator term. Thus the compensation provided is based upon all of these characteristics.

Detected mean velocity values are corrected by the mean velocity corrector 46 through a process based on a representation of the received spectrum as a convolution of the signal received at one element with a distortion function based on the array aperture. The ideal spectrum is given by $$h(t) = \exp[j2\pi ft] \qquad (3)$$

where f is computed from the frequency shift equation (1). The distortion function represents the separate Doppler angles $\theta_r$ and $\theta_x$ of each transducer element of the receive and transmit apertures, respectively, and is expressed as $$c(t) = \sum_r \left( W_r \sum_x \exp\left[ j\pi f \frac{(\cos\theta_x + \cos\theta_r - 2\cos\theta)}{\cos\theta} t \right] \right) \qquad (4)$$

where $W_r$ is the receive aperture weighting, or apodization, function and $\theta$ is the nominal Doppler angle. If desired the weighting function of both the transmit and receive apertures can be represented. From equations (3) and (4) it is seen that the distortion function can be written as $$c(t) = \sum_r \left( W_r \sum_x h(a_{rx}t) \right) \qquad (5)$$

where $$a_{rx} = \frac{(\cos\theta_x + \cos\theta_r - 2\cos\theta)}{2\cos\theta} \qquad (6)$$

The time domain signal corresponding to the ideal spectrum can then be represented by $$h(t) = \frac{g(t)}{\sum_r \left( W_r \sum_x h(a_{rx}t) \right)} \qquad (7)$$

where g(t) is the received Doppler signal. Using Fourier theory a corrected mean velocity value $<H(f)>$ is derived from equation (7) by $$<H(f)> = \frac{<G(f)>}{\left[ 1 + \frac{\left\{ \sum_r \left( W_r \sum_x a_{rx} \right) \right\}}{n_x \sum_r W_r} \right]} \qquad (8)$$

where $<G(f)>$ is the uncorrected mean velocity value produced by mean velocity detector 44 and $n_x$ is the number of transducer elements in the transmit aperture.

It is seen from equation (67) that the correction of mean velocity values is based upon the five factors identified above as the basis for peak velocity compensation.

The premise for correction of mean velocity can be applied more generally to correct the entire Doppler spectrum for use of an array transducer. Since the spectrum of the received signals can be represented by the convolution of the ideal spectrum with an array distortion function, the ideal or corrected spectrum can be derived from the Doppler frequency estimation information by deconvolving the received signal spectrum with the array distortion function using the processes and transformations of equations (3)–(7).

Figure 5:
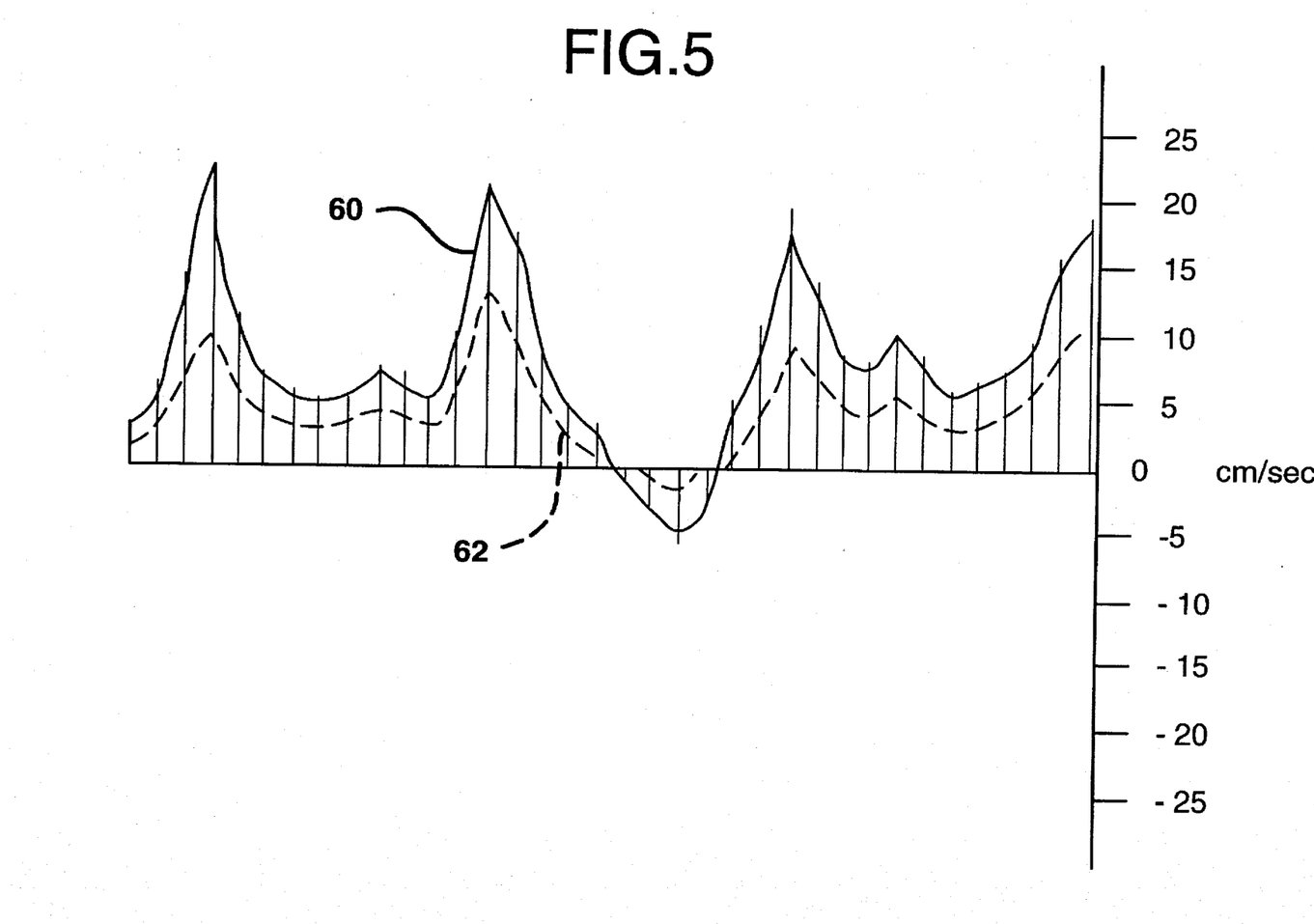
FIG. 5 is a spectral Doppler display highlighting peak and mean velocities.

A typical spectral Doppler display which uses the corrected peak and mean velocity values is shown in FIG. 5. The spectral display of FIG. 5 typically scrolls in real time across the display monitor 52 from right to left across the screen. New spectral lines are continually appearing at the right side of the display, and old lines from previous heart cycles disappear as they reach the left side of the display. In the example of FIG. 5, each spectral (vertical) line indicates the range of flow velocities existing at a particular moment at the sample volume site in the body. The corrected peak velocity values are at the peak of each spectral line and are shown connected by a line 60 in the drawing. The corrected mean velocity values of the spectral lines are connected by the dashed line 62. Thus, an arrangement of the present invention can provide accurate clinical information in a real time display.

Figure 6:
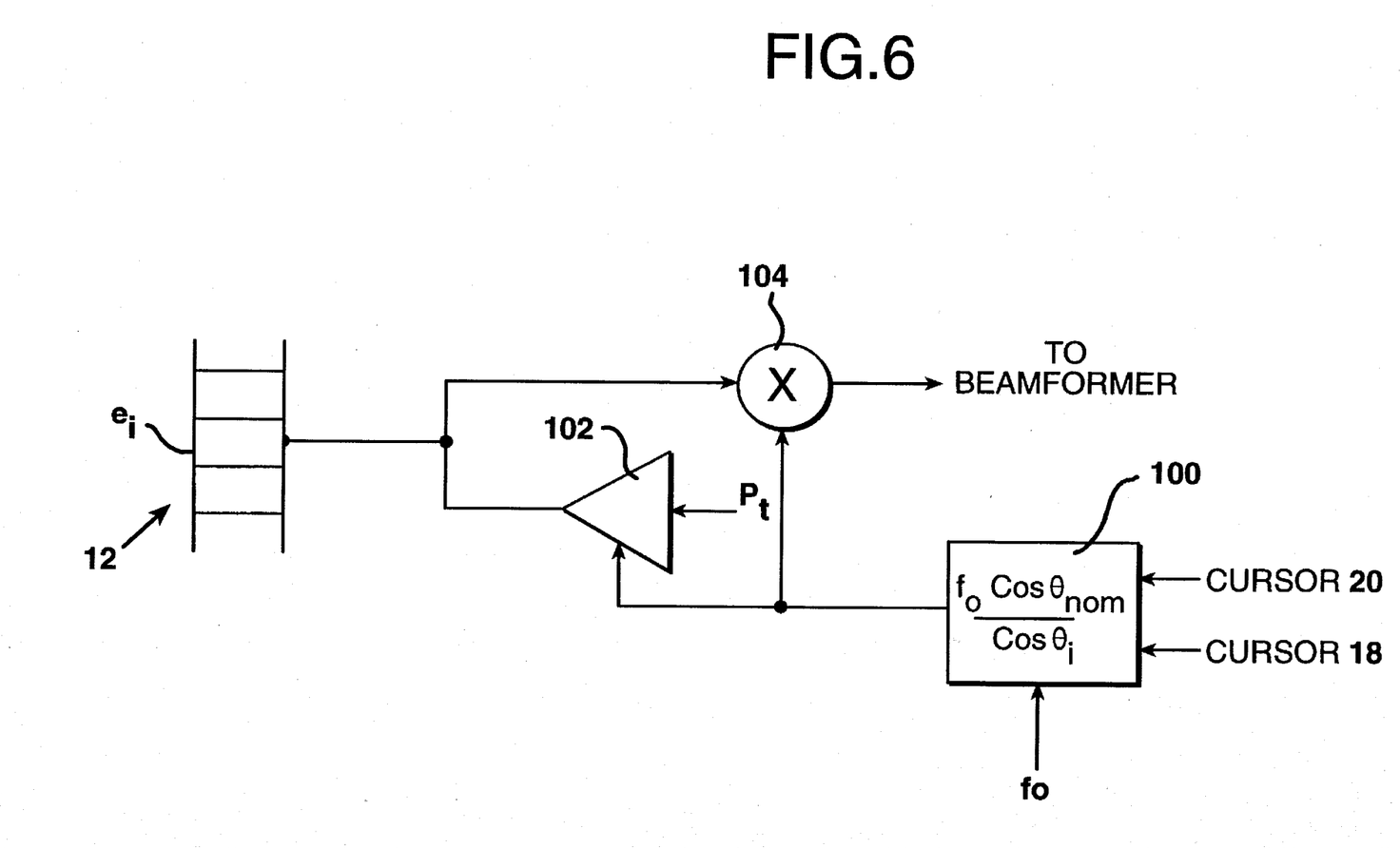
FIG. 6 illustrates a technique for compensating for spectral broadening by use of a unique reference frequency for each transducer element of a transducer array.

As discussed above, the problem of spectral broadening arises by reason of transmission and reception of Doppler signals in differing angular relationships to flow at elements across the transducer aperture. The compensating arrangement of FIG. 1 advantageously corrects for the problem after all of the individual element signals have been combined by beamforming to form coherent echo signals and after the estimation of Doppler frequencies. The arrangement also lends itself well to embodiment in software in the digital domain. An alternative technique for providing spectral broadening compensation is shown in FIG. 6, which is performed on an element by element basis. In the conventional transmission and reception of Doppler signals, the transmitted signals exhibit a narrow Doppler spectrum having a center frequency $f_o$. The received Doppler echo signals are detected with the $f_o$ frequency as a reference. To account for the differing phase relationships of Doppler signals across the aperture of an array transducer, this alternative technique provides a phase adjustment to this reference signal which is based upon the location of each element in the array. For a transducer array with transducers 1 through n, the $i^{th}$ transducer $e_i$ uses a Doppler reference signal of the form $$\frac{f_o \cos\theta_{nom}}{\cos\theta_i} \quad (9)$$

where $\theta_i$ is the Doppler angle of the $i^{th}$ transducer element. In FIG. 2 for example the Doppler angle of transducer element $e_n$ is $\theta_{xmt}$; the Doppler angle of transducer $e_{rcvn}$ is $\theta_{rcv}$. Thus, the $\cos\theta_i$ term provides a unique phase reference for each transducer element of the array based upon its unique position along the array.

An arrangement embodying this alternative technique is shown in FIG. 6. A transducer element $e_i$ of transducer array 12 transmits a Doppler wave when activated by a pulser 102. The pulser 102 transmits the reference signal produced by reference signal generator 100 when gated by a transmit gating pulse $P_t$. Received Doppler echo signals are provided to a detector or mixer 104, where they are detected or shifted with reference to the same reference signal. The illustrated arrangement is repeated for each transducer element so that each element will operate with a Doppler reference signal specifically tailored to its position in the array and its relationship to the sample volume being interrogated.

As shown above, the $\theta_{nom}$ term is known from knowledge of the positioning of cursors 18 and 20 with respect to the sample volume and blood flow. The positioning of the cursors also provides in a similar manner the information needed to compute a unique Doppler angle $\theta_i$ and cosine term for each element along the transducer array. Thus, once the cursors are set, precisely determined Doppler reference signals can be used for each element of the array. Unique reference signals can be used during either transmission or reception, but in a preferred embodiment the unique reference signals are used for both transmission and reception as shown in FIG. 6.

The principles of the present invention are applicable to other techniques of velocity estimation that are not strictly based on a Doppler frequency shift, such as time domain velocity determination techniques. In such techniques, successively received time domain signals are used to develop frequency estimations through correlation processing. Such techniques are susceptible to spectral broadening effects, which may be compensated by the techniques of the present invention.

What is claimed is:

1. In an ultrasonic diagnostic imaging system including Doppler apparatus for making ultrasonic measurements of flow conditions at a sample volume within the body comprising:

an array transducer having multiple elements comprising an active aperture of a given dimension;

a receiver coupled to said array transducer for receiving echo signals from elements of the transducer aperture;

a Doppler processor coupled to said receiver for Doppler processing of echo signals received from said sample volume to develop estimates of flow velocity at said sample volume;

a peak velocity detector coupled to said Doppler processor for identifying a peak flow velocity from a number of said flow velocity estimates, including means for identifying said peak flow velocity as a function of said dimension of said active aperture of said transducer array and the location of said sample volume with respect to said active aperture; and a display for displaying said identified peak flow velocity.

2. The ultrasonic diagnostic imaging system of claim 1, wherein said means for identifying comprises means for identifying said peak flow velocity in relation to the smallest Doppler angle extant between ones of said elements of said array and the direction of flow at said sample volume.

3. The ultrasonic diagnostic imaging system of claim 2, wherein said display includes means for displaying said sample volume in relation to said transducer array, and means for locating a cursor which indicates the direction of flow at said sample volume.

4. The ultrasonic diagnostic imaging system of claim 3, wherein said means for identifying comprises means for identifying the smallest angle extant between said cursor and each of the paths extending from said sample volume to each of said transducer elements.

5. The ultrasonic diagnostic imaging system of claim 2, wherein said means for identifying further comprises means for identifying a nominal Doppler angle between said array transducer and said direction of flow at said sample volume.

6. The ultrasonic diagnostic imaging system of claim 1, wherein said peak velocity detector comprises means for identifying an initial peak flow velocity from a number of said flow velocity estimates; means for producing a peak velocity correction factor which is a function of a nominal Doppler angle with respect to said active aperture and a minimal Doppler angle with respect to said active aperture; and means for modifying said initial peak flow velocity in accordance with said correction factor.

7. The ultrasonic diagnostic imaging system of claim 6, wherein said correction factor is a function of the cosine of said nominal Doppler angle with respect to an active aperture of said array, and of the cosines of said minimal Doppler angles with respect to the transmit and receive apertures of said array.

8. The ultrasonic diagnostic imaging system of claim 7, wherein said correction factor is of the form $$\frac{2\cos\theta_{nom}}{(\cos\theta_{rcv} + \cos\theta_{xmt})}.$$

9. In an ultrasonic diagnostic imaging system including Doppler apparatus for making ultrasonic measurements of flow conditions within the body comprising:

an array transducer having multiple transducer elements;

a receiver coupled to said array transducer for receiving echo signals from elements of the transducer array;

a Doppler processor coupled to said receiver for Doppler processing of said echo signals to develop estimates of flow velocity at a sample volume within said body;

a mean velocity detector coupled to said Doppler processor for identifying a mean flow velocity from a number of flow velocity estimates, including means for identifying said mean flow velocity as a function of a spectral distortion function based upon the use of an array transducer; and a display for displaying said identified mean flow velocity.

10. The ultrasonic diagnostic imaging system of claim 9, wherein said mean velocity detector comprises means for identifying an initial mean flow velocity from a number of flow velocity estimates; and means for combining said initial mean flow velocity with a function that is based upon an ideal Doppler frequency spectrum and an array distortion function.

11. The ultrasonic diagnostic imaging system of claim 10, wherein said array distortion function is a function of the Doppler angles of each transducer element which receives an echo signal.

12. The ultrasonic diagnostic imaging system of claim 9, wherein said mean velocity detector comprises means for identifying an initial mean flow velocity from a number of flow velocity estimates; and means for modifying said initial mean flow velocity with a function that is based upon the weighting of the Doppler signals and a range of Doppler angles exhibited by the array.

13. In an ultrasonic diagnostic imaging system including Doppler apparatus for making ultrasonic measurements of flow conditions at a sample volume within the body comprising:

an array transducer having multiple transducer elements;

a transmitter coupled to said transducer elements for separately exciting said elements to produce transmitted Doppler signals;

a receiver coupled to said transducer elements for separately receiving Doppler signals from said sample volume; and a reference signal generator, coupled to said transmitter or receiver, for providing different Doppler reference signals to separate ones of said transmitted or received Doppler signals which are a function of the locations of the transducer elements which transmitted or received said Doppler signals and of the location of said sample volume with respect to said array transducer.

14. The ultrasonic diagnostic imaging system of claim 13, wherein said reference signal generator comprises means for providing different Doppler reference signals which are a function of the Doppler angles of elements of said array with respect to flow at said sample volume.

15. The ultrasonic diagnostic imaging system of claim 14, further including a display for displaying said sample volume in relation to said transducer array, and means for displaying a cursor which indicates the direction of flow at said sample volume; wherein said reference signal generator includes means for determining Doppler angles between elements of said array and said direction of flow.

16. The ultrasonic diagnostic imaging system of claim 15, wherein said display further includes means for displaying a nominal Doppler path between said array and said sample volume; and wherein said reference signal generator further includes means for determining the Doppler angle between said nominal Doppler path and said direction of flow.

17. The ultrasonic diagnostic imaging system of claim 16, wherein said reference signal generator provides Doppler reference signals of the form $$\frac{f_o \cos\theta_{nom}}{\cos\theta_i}$$

where $f_o$ is a nominal Doppler frequency, $\theta_{nom}$ is said Doppler angle between said nominal Doppler path and said direction of flow, and $\theta_i$ is the Doppler angle of the $i^{th}$ transducer element.

18. In an ultrasonic diagnostic imaging system including Doppler apparatus for making ultrasonic measurements of flow conditions at a sample volume within the body comprising:

an array of transducer elements;

a transmitter coupled to said transducer elements for separately exciting said elements to produce transmitted Doppler signals;

a receiver including demodulators coupled to respective ones of said transducer elements for separately receiving Doppler signals from said sample volume; and a reference signal generator, coupled to said receiver, for providing different Doppler reference signals to respective ones of said demodulators which are a function of the locations of the transducer elements in said array.

19. The ultrasonic diagnostic imaging system of claim 18, wherein said demodulators comprise mixers for demodulating received Doppler signals in relation to said Doppler reference signals.

20. The ultrasonic diagnostic imaging system of claim 18, wherein said reference signal generator is further coupled to said transmitter to produce transmitted Doppler signals which are functions of said Doppler reference signals.

21. The ultrasonic diagnostic imaging system of claim 18, wherein said reference signal generator provides Doppler reference signals which are a function of the locations of the transducer elements in said array with respect to the location of said sample volume.

22. The ultrasonic diagnostic imaging system of claim 21, wherein said reference signal generator is further coupled to said transmitter to produce transmitted Doppler signals which are functions of said Doppler reference signals.

23. In an ultrasonic diagnostic imaging system including Doppler apparatus for making ultrasonic measurements of flow conditions at a sample volume within the body comprising:

an array of transducer elements;

a transmitter coupled to said transducer elements for separately exciting said elements to produce transmitted Doppler signals;

a receiver including demodulators coupled to respective ones of said transducer elements for separately receiving Doppler signals from said sample volume; and a reference signal generator, coupled to said transmitter, for providing different Doppler reference signals to respective ones of said transducer elements which are a function of the locations of the transducer elements in said array.

24. The ultrasonic diagnostic imaging system of claim 23, wherein said transmitter includes a plurality of transducer pulsers coupled to respective ones of said transducer elements and responsive to said reference signal generator for exciting respective ones of said transducer elements in response to said Doppler reference signals.

25. The ultrasonic diagnostic imaging system of claim 23, wherein said reference signal generator provides Doppler reference signals which are a function of the locations of the transducer elements in said array with respect to the location of said sample volume.

26. In an ultrasonic diagnostic imaging system including Doppler apparatus for making ultrasonic measurements of flow conditions within the body comprising:

an array transducer having multiple transducer elements;

a receiver coupled to said array transducer for receiving echo signals from elements of the transducer array;

a Doppler processor coupled to said receiver for Doppler processing of said echo signals to develop estimates of flow velocity at a sample volume within said body;

a Doppler spectral processor, responsive to said Doppler processor, for combining the velocity estimates developed from said received signals with an array distortion function to produce velocity estimates exhibiting a modified spectrum; and a display for displaying said modified flow velocity estimates.

27. The ultrasonic diagnostic imaging system of claim 26, wherein said Doppler spectral processor comprises means for deconvolving the received signal spectrum with an array distortion function to produce a corrected signal spectrum.

* * * * *